United States Patent
Avila, Sr. et al.

(10) Patent No.: US 6,841,723 B2
(45) Date of Patent: Jan. 11, 2005

(54) ROMAINE LETTUCE VARIETY NAMED SUNBELT

(75) Inventors: Tony M. Avila, Sr., Salinas, CA (US); Adolfo Mederos, Salinas, CA (US)

(73) Assignee: Central Valley Seeds, Inc., Salinas, CA (US)

( * ) Notice: Subject to any disclaimer, the term of this patent is extended or adjusted under 35 U.S.C. 154(b) by 44 days.

(21) Appl. No.: 10/338,284

(22) Filed: Jan. 7, 2003

(65) Prior Publication Data

US 2004/0133950 A1 Jul. 8, 2004

(51) Int. Cl.$^7$ .............................. A01H 1/00; A01H 4/00; A01H 5/00; A01H 5/10; C12N 15/82
(52) U.S. Cl. ..................... 800/305; 435/410; 800/260; 800/278; 800/279; 800/298; 800/300; 800/301; 800/302
(58) Field of Search ........................ 435/410; 800/260, 800/266, 278, 298, 279, 305, 300, 301, 302

(56) References Cited

U.S. PATENT DOCUMENTS 5,850,009 A * 12/1998 Kevern ..................... 800/271
6,689,941 B2 * 2/2004 Waycott .................... 800/305

OTHER PUBLICATIONS

De Vries et al 1994, Plant Systematics and Evolution 193: 125–141.*

* cited by examiner

*Primary Examiner*—David H Kruse
(74) *Attorney, Agent, or Firm*—Jondle & Associates P.C.

(57) ABSTRACT

A novel romaine lettuce cultivar, designated Sunbelt, is disclosed. The invention relates to the seeds of lettuce cultivar Sunbelt, to the plants of lettuce line Sunbelt and to methods for producing a lettuce plant by crossing the cultivar Sunbelt with itself or another lettuce (*Lactuca* sp.) line. The invention further relates to methods for producing a lettuce plant containing in its genetic material one or more transgenes and to the transgenic plants produced by that method and to methods for producing other lettuce lines derived from the cultivar Sunbelt.

16 Claims, No Drawings

ROMAINE LETTUCE VARIETY NAMED SUNBELT

BACKGROUND OF THE INVENTION

The present invention relates to a new and distinctive Romaine lettuce (*Lactuca sativa*) variety, designated Sunbelt.

*Lactuca sativa*, L., commonly known as lettuce is an increasingly popular vegetable not only in the United States but also around the world. A large number of different cultivars and varieties of lettuce have been bred and are now grown all over. These cultivars fall into four main classes, mainly based on their shape and growth style. These four classes of *Lactuca sativa*, L. are regarded as Romaine or Cos, Leaf, Butterhead and Crisphead (also known as Iceberg) lettuce.

Although usually consumed fresh, lettuce is eaten more frequently than any other vegetable and makes up a basic ingredient in salads or other food items and used as a mix with other fresh vegetables. Lettuce can also be used as a garnish for its fresh color and crisp leaf texture. Nutritionally, lettuce is an abounded source of vitamins, minerals and anti oxidants. In fact, the darker the green leaf color, the more nutritious and healthful. Amongst all the lettuce types, the romaine or Cos type is believed to be the most nutritious of all lettuces and is an excellent source of vitamin C. The romaine type lettuce is rather unique because it grows upright producing a cylindrical shaped head. In general, the leaf color is a medium to light green color with a creamy interior. In the United States lettuce with darker green leaf color is preferred.

Superior romaine lettuce varieties are highly desirable in the lettuce field industry. An improved lettuce may generally exhibit increased weight and yield, display field resistance to various important lettuce diseases, higher seed yield, vigorous seed, tolerance to drought and heat, and present genetic uniformity with a darker green leaf color, thick leaf texture and with superior holding and shipping quality.

There are numerous steps in the development of any novel, desirable plant germplasm. Plant breeding begins with the analysis and definition of problems and weaknesses of the current germplasm, the establishment of program goals, and the definition of specific breeding objectives. The next step is the selection of germplasm that possess the traits to meet the program objectives, market and consumer demands. The overall goal is to combine in a single variety or hybrid an improved combination of desirable traits from the available parental germplasm.

*Lactuca sativa* is in the Cichoreae tribe of the Asteraceae (Compositae family). Lettuce is related to chicory, sunflower, aster, dandelion, artichoke and chrysanthemum. *Sativa* is one of about 300 species in the genus *Lactuca*. There are seven different morphological types of lettuces: the Crisphead group includes the iceberg and Batavian types. Iceberg lettuce forms a firm spherical head that is tightly formed with brittle textured foliage with a white or creamy yellow green interior. The Batavian lettuce predates the iceberg type and has a smaller and less firm head. The Butterhead group has a small, soft head with an almost oily texture. The Romaine, also known as Cos lettuce, has elongated upright leaves forming a loose, loaf shaped head. The outer leaves are usually dark green. The Leaf lettuces comes in many varieties, none of which form a head. The next three types are seldom seen in the United States: Latin lettuce looks like a cross between romaine and butterhead; stem lettuce has long, narrow leaves and thick, edible stems. Oilseed lettuce, finally, is a primitive type grown for its large seeds that are pressed to obtain oil.

*Lactuca sativa* is a diploid species with nine pairs of chromosomes (2n=2x=18). Lettuce is an obligate self-pollinating species. This means that the pollen is shed before stigma emergence, assuring 100% self-fertilization.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar (s). If a single observation is inconclusive, replicated observations provide a better estimate of its genetic worth.

The goal of plant breeding is to develop new, unique and superior lettuce cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same lettuce traits.

Each year, the plant breeder selects the germplasm to advance to the next generation. This germplasm is grown under unique and different geographical, climatic and soil conditions, and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior lettuce cultivars.

The development of commercial lettuce cultivars requires the development of lettuce varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits, are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follow in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population, will be represented by a progeny when generation advance is completed Descriptions of other breeding methods that are commonly used for different traits and crops can be found in one of several reference books (e.g., *Principles of Plant Breeding* John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce high quality seeds easily and economically.

Lettuce in general and romaine lettuce in particular is an important and valuable vegetable crop. Thus, a continuing goal of plant breeders is to develop stable, high yielding lettuce cultivars that are agronomically sound. The reasons for this goal are obviously to maximize the amount of yield produced on the land. To accomplish this goal, the lettuce breeder must select and develop lettuce plants that have the traits that result in superior cultivars.

SUMMARY OF THE INVENTION

According to the invention, there is provided a novel romaine lettuce cultivar designated Sunbelt. This invention thus relates to the seeds of lettuce cultivar Sunbelt, to the plants of lettuce cultivar Sunbelt and to methods for producing a lettuce plant produced by crossing the lettuce Sunbelt with itself or another lettuce (*Lactuca* sp.) line, and to methods for producing a lettuce plant containing in its genetic material one or more transgenes and to the transgenic lettuce plants produced by that method. This invention also relates to methods for producing other lettuce cultivars derived from lettuce cultivar Sunbelt and to the lettuce cultivar derived by the use of those methods. This invention further relates to hybrid lettuce seeds and plants produced by crossing the line Sunbelt with another lettuce line.

In another aspect, the present invention provides regenerable cells for use in tissue culture of lettuce cultivar Sunbelt. The tissue culture will preferably be capable of regenerating plants having the physiological and morphological characteristics of the foregoing lettuce plant, and of regenerating plants having substantially the same genotype as the foregoing lettuce plant. Preferably, the regenerable cells in such tissue cultures will be somtic and non-somatic tissues such as embryos, protoplasts, seeds, callus, pollen, leaves, anthers, roots, and meristematic cells. Still further, the present invention provides lettuce plants regenerated from the tissue cultures of the invention.

Another objective of the invention is to provide methods for producing other lettuce plants derived from lettuce cultivar Sunbelt. Lettuce cultivars derived by the use of those methods are also part of the invention.

The invention also relates to methods for producing a lettuce plant containing in its genetic material one or more transgenes and to the transgenic lettuce plant produced by that method.

In another aspect, the present invention provides for single gene converted plants of Sunbelt. The single transferred gene may preferably be a dominant or recessive allele. Preferably, the single transferred gene will confer such trait as male sterility, herbicide resistance, insect resistance, resistance for bacterial, fungal, or viral disease, male fertility, enhanced nutritional quality and industrial usage. The single gene may be a naturally occurring lettuce gene or a transgene introduced through genetic engineering techniques.

The invention further provides methods for developing lettuce plant in a lettuce plant breeding program using plant breeding technique including recurrent selection, backcrossing, pedigree breeding, restriction fragment length polymorphism (RFLP) enhanced selection, genetic marker development, selection and transformation. Seeds, lettuce plant, and parties thereof produced by such breeding methods are also part of the invention.

DEFINITIONS

In the description and tables which follow, a number of terms are used. In order to provide a clear and consistent understanding of the specification and claims, including the scope to be given such terms, the following definitions are provided:

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics, except for the characteristics derived from the converted gene.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of a line are recovered in addition to the single gene transferred into the line via the backcrossing technique or via genetic engineering. This is also referred to as essentially derived concept.

Maturity Date. Maturity refers to the stage when the plants are of full size or optimum weight, in marketable form or shape to be of commercial or economic value. In romaine types they range from 60–95 days from time of seeding or watering (wet) date, depending upon the season of the year.

Plant Tissue Color Chart. Refers to the Munsell Color Chart for Plant Tissue which publishes an official botanical color chart quantitatively identifying colors according to a defined numbering system, The Munsell Color Chart for Plant Tissue may be purchased from Munsell Color Services, 617 Little Britain Road, Suite 102, New Windsor, N.Y. 12553-6148, USA, Part Number: 50150.

Lettuce Yield (Tons/Acre). The yield in tons/acre is the actual yield of the lettuce at harvest.

Total Leaf Count: The total number of leaves per marketable trimmed plant at harvest stage.

Leaf Length Index: Differences in the leaf shape between the two varieties. This is calculated by dividing the total leaf length by the leaf width.

DETAILED DESCRIPTION OF THE INVENTION

Lettuce cultivar Sunbelt has superior characteristics and was developed from a hand pollinated cross of a single romaine variant of a crisphead 'Target' (Plant Variety Protection Number 8900102, Arthur Yates and Company Pty. Ltd.) variety, 'Darkland Cos' (Plant Variety Protection Number 9000137, Central Valley Seeds, Inc.) romaine lettuce and the lettuce romaine variety 'Augustus' (Plant Variety Protection Number 9200010, Seminis Vegetable Seeds, Inc.).

The cultivar Sunbelt is similar to 'King Henry' however there are numerous differences as shown in the table below:

| Characteristic | 'Sunbelt' | 'King Henry' |
| --- | --- | --- |
| Leaf Blistering (Savoyedness) | Slight | Moderate-Heavy |
| Maturity | About 2–3 Days Early | About 2–3 Days Late |
| Tipburn | Highly Resistant | Intermediate |
| Leaf Undulation | Slight | Smooth |
| Cupping | Non-cupping | Intermediate |
| Leaf Fringe Burn | Resistant | Susceptible |
| Leaf Color | Value 4 Chroma 4 Hue 5 GY | Value 4 Chroma 8 Hue 5 GY |

Sunbelt belongs to the cutting/leaf type lettuce, *Lactuca sativa* L. varieties. Sunbelt is adapted for the lettuce growing regions of California and Arizona. Sunbelt is relatively medium in height, with a large frame structure, very thick and slight savoy (blistering) leaf texture, medium-dark green leaf color, short core length, and tapered to a flat butt shape with smooth midribs. Sunbelt expresses field resistance to leaf tip burn, fringe burn, corky root disease (*Rhizomonas suberifaciens*) and downy mildew (*Bremia lactucae*). According to the Munsell Color Chart for Plant Tissues, Sunbelt has a leaf color value 4 chroma 4 hue 5 GY. Sunbelt is genetically pure and stable and has excellent seed emergency.

Some of the criteria used to select in various generations include: color, disease resistances, plant weight, number of leaves, resistance to leaf tip burn and fringe burns, appearance and length, yield, emergence, maturity, plant architecture, and seed yield and quality.

The cultivar has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in Sunbelt.

Lettuce cultivar Sunbelt has the following morphologic and other characteristics (based primarily on data collected at Salinas, Calif. Research Station).

| VARIETY DESCRIPTION INFORMATION | |
| --- | --- |
| PLANT TYPE: | |
| | Cos or Romaine |
| SEED: | |
| Seed Color | Black (Gray Brown) |
| Light Dormancy | Not Required |
| Heat Dormancy | Susceptible |

-continued

COTYLEDONS:

| | |
|---|---|
| Shape of Cotyledons | Broad |
| Shape of Fourth Leaf | |
| Index of Fourth Leaf (L/W X 10) | |
| Apical Margin | Finely Denthate |
| Basal Margin | Moderately Dentate |
| Undulation | Flat |
| Green Color | Dark Green |
| Anthocyanin | Absent |
| Distribution | None |
| Rolling | Absent |
| Cupping | Uncupped |
| Reflexing | None |

MATURE LEAVES

Margin:

| | |
|---|---|
| Incision Depth (Deepest penetration of the margin) | Absent/Shallow |
| Indentation (Finest Division of the Margin) | Entire |
| Undulation of the Apical Margin | Absent/Slight |
| Green Color | Dark Green |

ANTHOCYANIN

| | |
|---|---|
| Distribution | Absent |
| Concentration | None |
| Size | Medium |
| Glossiness | Glossy |
| Blistering | Moderate |
| Leaf Thickness | Thick |
| Trichomes | Absent |

| | Sunbelt | King Henry |
|---|---|---|
| PLANT: | | |
| Spread of Frame Leaves | 17.3 cm | 15.9 cm |
| Head Diameter (market trimmed with single cup leaf) | NA | NA |
| Head Shape | Non-Heading | Non-Heading |
| Head Size Class | Medium | Medium |
| Head Count per Carton | 24 | 24 |
| Head Weight (Avg.) | 834 g | 702 g |
| Head Firmness | Lose | Lose |
| BUTT: | | |
| Butt Shape | Round | Round |
| Midrib | Flattened | Flattened |
| CORE (Stem of market-trimmed head) | | |
| Diameter at the based of the head | 3.98 cm | 3.89 cm |
| Ratio of the Head Diameter/Core Diameter | NA | NA |
| Core Height from base of Head to Apex | 5.61 cm | 5.79 cm |
| BOLTING: | | |
| Number of Days from First Water Date to Seeds Stock Emergence (Summer Condition) | 75 | 73 |
| Bolting Class | Slow | Slow |
| Height of Mature Seeds Stock | 86.4 cm | 91.4 cm |
| Speared of Bolter Leaves | 27.9 cm | 24.1 cm |
| Bolter Leaves | Curved | Curved |
| Margin | Dentate | Dentate |
| Color | Dark Green | Medium Green |
| BOLTER HABIT: | | |
| Terminal inflorescence | Present | Present |
| Lateral Shoots (above head) | Present | Present |
| Basal Side Shoots | Present | Present |
| MATURITY (Earliness of harvest-mature head formation in days from first water date) | | |
| Season | | |
| Spring | 110 | 113 |
| Summer | 68 | 70 |
| Fall | 74 | 76 |
| Winter | NA | NA |
| Suggested Planting Date (s), and Location (s): | | |
| Spring | Yuma, AZ | NA |
| | CA Desert Regions | |
| | Huron, CA | |
| | Five Points, CA | |
| Summer | Salinas, CA | NA |
| | King City, CA | |
| | Green Field, CA | |
| | Hollister, CA | |
| Fall | Yuma, AZ | NA |
| | CA Desert Regions | |
| | Huron, CA | |
| | Five Points, CA | |
| Winter | NA | NA |
| ADAPTATION (Primary regions of adaptation, tested and proven) | | |
| Adaptation Regions | Salinas Valley, CA Huron, CA Yuma, AZ | NA Huron, CA Yuma, AZ |
| Southwest (CA & AZ desert) | Adapted | NA |
| West Coast | Adapted | NA |
| Northeast | Not Tested | NA |
| North Central | Not Tested | NA |
| Southeast | Not Tested | NA |
| Greenhouse: | Not Tested | NA |
| Soil Type | Mineral/Organic | Both |
| DISEASES AND STRESS REACTIONS | | |
| VIRUS | | |
| Big Vein | Intermediate | NA |
| Lettuce Mosaic | Susceptible | NA |
| Cucumber Mosaic | Susceptible | NA |
| Broad Bean Wilt | Not Tested | NA |
| Turnip Mosaic | Not Tested | NA |
| Beat Western Yellows | Susceptible | NA |
| Lettuce Infectious Yellows | Susceptible | NA |
| FUNGI/BACTERIA | | |
| Root Rot (Pythium Root Rot) | NA | NA |
| Corky Root Rot (Rhizomonas suberifaciens) | Resistant | |
| Downy Mildew (Races I, IIA, III) | CA IIA | NA |
| Powdery Mildew | Not Tested | NA |
| Sclerotinia Rot | Intermediate | Susceptible |
| Bacterial Soft Rot (Pseudomonas spp. & others) | Not Tested | NA |
| Botrytis (Gray Mold) | Susceptible | NA |
| INSECTS | | |
| Cabbage Loopers | Susceptible | NA |
| Root Aphids | Susceptible | NA |
| Green Peach Aphid | Susceptible | NA |
| PHYSIOLOGICAL/STRESS | | |
| STRESS | | |
| Tipburn | Highly Resistant | Susceptible |
| Heat | Resistant | NA |
| Drought | Not Tested | NA |
| Cold | Resistant | NA |
| Salt | Not Tested | NA |
| Brown Rib (Rib Discoloration, Rib Blight) | NA | NA |
| POST HARVEST Characteristic | | |
| Pink Rib | Resistant | NA |
| Russet Spotting | Not Tested | NA |

| -continued | | |
|---|---|---|
| Rusty Brown | Not Tested | NA |
| Discoloration Internal Rib Necrosis (Blackheart, Gray Rib, Gray Streak) | Not Tested | NA |
| Brown Stain | Not Tested | NA |

FURTHER EMBODIMENTS OF THE INVENTION

This invention also is directed to methods for producing a lettuce cultivar plant by crossing a first parent lettuce plant with a second parent lettuce plant wherein either the first or second parent lettuce plant is a lettuce plant of the line Sunbelt. Further, both first and second parent lettuce plants can come from the cultivar Sunbelt. Still further, this invention also is directed to methods for producing a cultivar Sunbelt-derived lettuce plant by crossing cultivar Sunbelt with a second lettuce plant and growing the progeny seed, and repeating the crossing and growing steps with the cultivar Sunbelt-derived plant from 0 to 7 times. Thus, any such methods using the cultivar Sunbelt are part of this invention: selfing, backcrosses, hybrid production, crosses to populations, and the like. All plants produced using cultivar Sunbelt as a parent are within the scope of this invention, including plants derived from cultivar Sunbelt. Advantageously, the cultivar is used in crosses with other, different, cultivars to produce first generation ($F_1$) lettuce seeds and plants with superior characteristics.

As used herein, the term plant includes plant cells, plant protoplasts, plant cell tissue cultures from which lettuce plants can be regenerated, plant calli, plant clumps and plant cells that are intact in plants or parts of plants, such as embryos, pollen, ovules, flowers, seeds, roots, anthers, and the like.

As is well known in the art, tissue culture of lettuce can be used for the in vitro regeneration of a lettuce plant. Tissue culture of various tissues of lettuces and regeneration of plants therefrom is well known and widely published. For example, reference may be had to Teng et al., *HortScience*. 1992, 27: 9, 1030–1032 Teng et al., *HortScience*. 1993, 28: 6, 669–1671, Zhang et al., *Journal of Genetics and Breeding*. 1992, 46: 3, 287–290, Webb et al., *Plant Cell Tissue and Organ Culture*. 1994, 38: 1, 77–79, Curtis et al., *Journal of Experimental Botany*. 1994, 45: 279, 1441–1449, Nagata et al., *Journal for the American Society for Horticultural Science*. 2000, 125: 6, 669–672. It is clear from the literature that the state of the art is such that these methods of obtaining plants are, and were, "conventional" in the sense that they are routinely used and have a very high rate of success. Thus, another aspect of this invention is to provide cells which upon growth and differentiation produce lettuce plants having the physiological and morphological characteristics of variety Sunbelt.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as transgenes. Over the last fifteen to twenty years several methods for producing transgenic plants have been developed, and the present invention, in particular embodiments, also relates to transformed versions of the claimed line.

Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants, using transformation methods as described below to incorporate transgenes into the genetic material of the lettuce plant(s).

Expression Vectors for Lettuce Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., *Plant Physiol.* 86:1216 (1988), Jones et al., *Mol. Gen. Genet.*, 210:86 (1987), Svab et al., *Plant Mol. Biol.* 14:197 (1990<Hille et al., *Plant Mol. Biol.* 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galaetesidase, luciferase and chloramphenicol, acetyltransferase. Jefferson, R. A., *Plant Mol. Biol. Rep.* 5:387 (1987), Teeri et al., *EMBO J.* 8:343

(1989), Koncz et al., *Proc. Natl. Acad. Sci U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, Imagene Green™, p. 1–4 (1993) and Naleway et al.,*J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, promoter includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive promoter" is a promoter which is active under most environmental conditions.

A. Inducible Promoters

An inducible promoter is operably linked to a gene for expression in lettuce. Optionally, the inducible promoter is operably linked to a nucleotide sequence encoding a signal sequence which is operably linked to a gene for expression in lettuce. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3): 291–300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-specific or Tissue-preferred Promoters

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., Structure and Organization of Two Divergent Alpha-Amylase Genes from Barley,

*Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is lettuce. In another preferred embodiment, the biomass of interest is seed. For the relatively small number of transgenic plants that show higher levels of expression, a genetic map can be generated, primarily via conventional RFLP, AFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, AFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclose by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotoch. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hookworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung lettuce calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO95/16776 (disclosure of peptide derivatives of tachyolesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo α-1, 4-D-polygalacturonases facilitate fungal colonization and plant nutrient release by solubilizing plant cell wall homo-α-1, 4-D-galacturonase. See Lamb at al., *Bio/Technology* 10:1436 (1992). The cloning and characterization of a gene which encodes a lettuce endopolygalacturonase-inhibiting protein is described by Toubart et al., *Plant J.* 2:367 (1992).

R. A development-arrestive protein produced in nature by a plant. For example, Logemann et al., *Bioi/Technology* 10:305 (1992), have shown that transgenic plants expressing the barley ribosome-inactivating gene have an increased resistance to fungal disease.

R. A lettuce mosaic potyvirus (LMV) coat protein gene introduced into *Lactuca sativa* in order to increase its resistance to LMV infection. See Dinant et al., Molecular Breeding. 1997,3: 1, 75–86.

2. Genes that Confer Resistance to a Herbicide, for Example:

A. A herbicide that inhibits the growing point or meristem, such as an imidazalinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and *Streptomyces hygroscopicus* phosphinothricin-acetyl transferase, bar, genes), and pyridinoxy or phenoxy propionic acids and cyclohexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research.* 1999, 8: 1, 33–44 that discloses *Lactuca sativa* resistant to glufosinate. European patent application No. 0 333 033 to Kumada at al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., *Bio/Technology* 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., *Theor. Appl. Genet.* 83:435 (1992).

C. A herbicide that inhibits photosynthesis, such as a triazine (psbA and gs+ genes) and a benzonitrile (nitrilase gene). Przibilla et al., *Plant Cell* 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such as:

A. Increased iron content of the lettuce, for example by transforming a plant with a soybean ferritin gene as decribed in Goto et al., *Acta Horticulturae.* 2000, 521, 101–109. Parallel to the improved iron content enhanced growth of transgenic lettuces was also observed in early development stages.

B. Decreased nitrate content of leaves, for example by transforming a lettuce with a gene coding for a nitrate reductase. See for example Curtis et al., *Plant Cell Report.* 1999, 18: 11, 889–896.

C. Increased sweetness of the lettuce by transferring a gene coding for monellin, that elicits a flavor sweeter than sugar on a molar basis. See Penarrubia et al., *Biotechnology.* 1992, 10: 5, 561–564.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-mediated Transformation

One method for introducing an expression vector into plants is based on the natural transformation system of Agrobacterium. See, for example, Horsch et al., *Science* 227:1229 (1985). Curtis et al., *Journal of Experimental Botany.* 1994, 45: 279, 1441–1449, Torres et al., *Plant cell Tissue and Organic Culture.* 1993, 34: 3, 279–285, Dinant et al., *Molecular Breeding.* 1997, 3: 1, 75–86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Despite the fact the host range for Agrobacterium-mediated transformation is broad, some major cereal or vegetable crop species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, January), 165–169 (1993), Aragao, F. J. L., et al. *Plant Mol. Biol.* 20(2, October), 357–359 (1992), Aragao, F. J. L., et al. *Pl. Cell. Rep.* 12(9, July), 483–490 (1993). Aragao *Theor. Appl. Genet.* 93: 142–150 (1996), Kim, J.; Minamikawa, T. *Plant Science* 117: 131–138 (1996), Sanford et al., *Part. Sci. Technol.* 5:27 (1987), Sanford, J. C., *Trends Biotech,* 6:299 (1988), Klein et al., *Bio/Technology* 6:559–563 (1988), Sanford, J. C., *Physiol Plant* 7:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.,* 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, T. *Biologia Plantarum* 40(4): 507–514 (1997/98), Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994). See also Chupean et al., *Biotechnology.* 1989, 7: 5, 503–508.

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic lettuce line. Alternatively, a genetic trait that has been engineered into a particular lettuce cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term lettuce plant, cultivar or lettuce line is used in the context of the present invention, this also includes any single gene conversions of that line. The term single gene converted plant as used herein refers to those lettuce plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term backcrossing as used herein refers to the repeated crossing of a hybrid progeny back to one of the parental lettuce plants for that line. The parental lettuce plant that contributes the gene for the desired characteristic is termed the nonrecurrent or donor parent. This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a lettuce plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196; 5,948,957 and 5,969,212, the disclosures of which are specifically hereby incorporated by reference.

TABLES

'Sunbelt' is similar to 'King Henry'; however, 'Sunbelt' is significantly different than 'King Henry' based on the following measurements:

| Variable | Field Trial Location | No. Plants/ Rep | Rep No. | t*-value | P[t*] | Avg. 'Sunbelt' | Avg. 'King Henry' | LSD Mean 95% | Sigma |
|---|---|---|---|---|---|---|---|---|---|
| Plant Weight (g) | 1 | 15 | 1 | 2.408 | 0.003 | 470.0 | 394.6 | 69.94 | 80.20 |
| | | 15 | 2 | 2.123 | 0.018 | 416.7 | 320.0 | 101.81 | 131.73 |
| | 2 | 15 | 1 | 2.578 | 0.001 | 916.7 | 753.3 | 141.67 | 157.35 |
| | | 15 | 2 | 2.534 | 0.002 | 880.0 | 726.7 | 135.33 | 154.26 |
| | 3 | 15 | 1 | 1915 | 0.026 | 585.3 | 489.3 | 112.08 | 139.64 |
| | | 15 | 2 | 2.982 | 0.000 | 621.0 | 498.0 | 98.73 | 110.78 |
| | 4 | 15 | 1 | 2.916 | 0.001 | 522.3 | 456.3 | 50.61 | 60.58 |
| | | 15 | 2 | 2.205 | 0.014 | 561.7 | 493.3 | 69.29 | 89.11 |
| | 5 | 15 | 1 | 2.303 | 0.011 | 752.7 | 678.3 | 72.16 | 93.79 |
| | | 15 | 2 | 2.544 | 0.004 | 747.7 | 652.3 | 83.79 | 103.76 |
| | 6 | 15 | 1 | 1.918 | 0.027 | 794.3 | 690.7 | 120.85 | 151.98 |
| | | 15 | 2 | 1.948 | 0.034 | 770.7 | 673.7 | 111.37 | 148.90 |
| | 7 | 15 | 1 | 2.136 | 0.018 | 1232.7 | 1086.7 | 152.84 | 197.63 |
| | | 15 | 2 | 3.032 | 0.000 | 1306.0 | 1006.7 | 220.74 | 240.70 |
| | 8 | 15 | 1 | 2.741 | 0.001 | 998.7 | 779.3 | 178.96 | 190.71 |
| | | 15 | 2 | 2.750 | 0.000 | 952.7 | 760.7 | 156.13 | 162.75 |
| | 9 | 15 | 1 | 1.788 | 0.031 | 1196.7 | 1052.0 | 180.88 | 217.15 |
| | | 15 | 2 | 1.869 | 0.036 | 1283.3 | 1134.0 | 178.65 | 231.67 |
| Leaf Width (cm) | 1 | 15 | 1 | 2.354 | 0.005 | 17.8 | 16.5 | 1.26 | 1.48 |
| | | 15 | 2 | 2.987 | 0.000 | 18.0 | 15.5 | 1.87 | 2.03 |
| | 2 | 15 | 1 | 2.163 | 0.007 | 17.8 | 16.8 | 1.09 | 1.22 |
| | | 15 | 2 | 3.011 | 0.000 | 18.2 | 16.6 | 1.09 | 1.16 |
| | 3 | 15 | 1 | 2.246 | 0.007 | 15.1 | 14.3 | 0.88 | 1.03 |
| | | 15 | 2 | 2.467 | 0.003 | 15.7 | 14.1 | 1.44 | 1.66 |
| | 4 | 15 | 1 | 2.270 | 0.008 | 14.5 | 13.5 | 1.01 | 1.23 |
| | | 15 | 2 | 2.610 | 0.002 | 14.1 | 12.9 | 0.94 | 1.11 |
| | 5 | 15 | 1 | 2.819 | 0.001 | 15.5 | 14.3 | 0.98 | 1.14 |
| | | 15 | 2 | 2.699 | 0.001 | 15.6 | 14.3 | 1.02 | 1.13 |
| | 6 | 15 | 1 | 2.006 | 0.014 | 17.6 | 16.4 | 1.26 | 1.48 |
| | | 15 | 2 | 2.755 | 0.001 | 18.1 | 16.7 | 1.08 | 1.16 |
| | 7 | 15 | 1 | 2.372 | 0.005 | 19.9 | 18.6 | 1.19 | 1.42 |
| | | 15 | 2 | 3.240 | 0.000 | 20.6 | 18.1 | 1.67 | 1.66 |
| | 8 | 15 | 1 | 1.788 | 0.024 | 18.9 | 17.4 | 1.80 | 2.06 |
| | | 15 | 2 | 1.605 | 0.034 | 18.2 | 16.9 | 1.84 | 2.02 |
| | 9 | 15 | 1 | 1.771 | 0.031 | 18.3 | 17.3 | 1.25 | 1.50 |
| | | 15 | 2 | 1.952 | 0.028 | 17.8 | 16.8 | 0.99 | 1.28 |
| Leaf Length (cm) | 1 | 15 | 1 | 1.791 | 0.025 | 29.5 | 31.1 | 1.91 | 2.19 |
| | | 15 | 2 | 1.934 | 0.019 | 30.9 | 32.1 | 1.41 | 1.68 |
| | 2 | 15 | 1 | 1.710 | 0.044 | 28.9 | 30.0 | 1.47 | 1.83 |
| | | 15 | 2 | 1.905 | 0.022 | 28.6 | 29.8 | 1.44 | 1.72 |
| | 3 | 15 | 1 | 2.088 | 0.028 | 22.5 | 23.6 | 1.16 | 1.60 |
| | | 15 | 2 | 2.143 | 0.012 | 22.1 | 23.3 | 1.19 | 1.46 |
| | 4 | 15 | 1 | 1.896 | 0.020 | 22.7 | 23.7 | 1.19 | 1.40 |
| | | 15 | 2 | 1.872 | 0.025 | 22.6 | 23.5 | 1.11 | 1.35 |
| | 5 | 15 | 1 | 1.390 | 0.034 | 23.6 | 24.8 | 1.59 | 1.84 |
| | | 15 | 2 | 1.670 | 0.028 | 23.7 | 24.6 | 1.25 | 1.44 |
| | 6 | 15 | 1 | 2.134 | 0.010 | 25.1 | 26.2 | 1.17 | 1.38 |
| | | 15 | 2 | 3.257 | 0.000 | 24.6 | 26.9 | 1.62 | 1.59 |
| | 7 | 15 | 1 | 3.088 | 0.000 | 25.6 | 28.1 | 1.83 | 1.92 |
| | | 15 | 2 | 3.431 | 0.000 | 25.8 | 28.2 | 1.54 | 1.44 |
| | 8 | 15 | 1 | 1.927 | 0.023 | 23.4 | 24.9 | 1.73 | 2.11 |
| | | 15 | 2 | 1.665 | 0.032 | 23.3 | 25.1 | 2.42 | 2.73 |
| | 9 | 15 | 1 | 1.852 | 0.019 | 25.9 | 27.3 | 1.60 | 1.83 |
| | | 15 | 2 | 1.934 | 0.032 | 24.2 | 25.8 | 1.84 | 2.41 |
| Total Leaf Count | 1 | 15 | 1 | 2.598 | 0.001 | 41.1 | 38.0 | 2.64 | 2.90 |
| | | 15 | 2 | 2.532 | 0.002 | 39.8 | 37.0 | 2.47 | 2.81 |
| | 2 | 15 | 1 | 2.175 | 0.007 | 52.9 | 47.9 | 5.14 | 5.85 |
| | | 15 | 2 | 2.746 | 0.001 | 54.2 | 49.7 | 3.69 | 4.40 |
| | 3 | 15 | 1 | 2.904 | 0.000 | 55.7 | 50.6 | 3.90 | 4.29 |
| | | 15 | 2 | 2.890 | 0.001 | 56.3 | 52.1 | 3.25 | 3.70 |
| | 4 | 15 | 1 | 2.942 | 0.000 | 51.2 | 47.7 | 2.63 | 2.94 |
| | | 15 | 2 | 2.836 | 0.000 | 52.5 | 48.2 | 3.36 | 3.54 |
| | 5 | 15 | 1 | 2.493 | 0.003 | 55.8 | 52.4 | 3.05 | 3.61 |
| | | 15 | 2 | 3.576 | 0.000 | 56.9 | 51.5 | 3.38 | 3.36 |
| | 6 | 15 | 1 | 2.055 | 0.010 | 59.5 | 57.1 | 2.54 | 2.86 |
| | | 15 | 2 | 2.492 | 0.005 | 58.1 | 54.3 | 3.47 | 4.29 |

TABLES-continued

'Sunbelt' is similar to 'King Henry'; however, 'Sunbelt' is significantly different than 'King Henry' based on the following measurements:

| Variable | Field Trial Location | No. Plants/ Rep | Rep No. | t*-value | P[t*] | Avg. 'Sunbelt' | Avg. 'King Henry' | LSD Mean 95% | Sigma |
|---|---|---|---|---|---|---|---|---|---|
| | 7 | 15 | 1 | N/A | | | | | |
| | | 15 | 2 | N/A | | | | | |
| | 8 | 15 | 1 | N/A | | | | | |
| | | 15 | 2 | N/A | | | | | |
| | 9 | 15 | 1 | N/A | | | | | |
| | | 15 | 2 | N/A | | | | | |
| Leaf Length Index | 1 | 15 | 1 | 2.842 | 0.001 | 1.67 | 1.89 | 0.176 | 0.195 |
| | | 15 | 2 | 3.080 | 0.000 | 1.73 | 2.10 | 0.265 | 0.268 |
| | 2 | 15 | 1 | 2.453 | 0.002 | 1.62 | 1.78 | 0.160 | 0.172 |
| | | 15 | 2 | 2.894 | 0.000 | 1.57 | 1.78 | 0.165 | 0.173 |
| | 3 | 15 | 1 | 2.791 | 0.001 | 1.48 | 1.66 | 0.135 | 0.158 |
| | | 15 | 2 | 3.119 | 0.000 | 1.42 | 1.66 | 0.176 | 0.175 |
| | 4 | 15 | 1 | 2.924 | 0.000 | 1.57 | 1.77 | 0.150 | 0.156 |
| | | 15 | 2 | 3.303 | 0.000 | 1.61 | 1.82 | 0.140 | 0.140 |
| | 5 | 15 | 1 | 3.658 | 0.000 | 1.52 | 1.74 | 0.130 | 0.124 |
| | | 15 | 2 | 3.224 | 0.000 | 1.52 | 1.72 | 0.139 | 0.139 |
| | 6 | 15 | 1 | 2.949 | 0.000 | 1.43 | 1.61 | 0.130 | 0.132 |
| | | 15 | 2 | 4.104 | 0.000 | 1.36 | 1.62 | 0.137 | 0.113 |
| | 7 | 15 | 1 | 3.952 | 0.000 | 1.29 | 1.52 | 0.126 | 0.115 |
| | | 15 | 2 | 4.219 | 0.000 | 1.26 | 1.56 | 0.161 | 0.120 |
| | 8 | 15 | 1 | 2.664 | 0.001 | 1.24 | 1.44 | 0.160 | 0.180 |
| | | 15 | 2 | 2.957 | 0.000 | 1.28 | 1.49 | 0.160 | 0.160 |
| | 9 | 15 | 1 | 2.945 | 0.000 | 1.42 | 1.58 | 0.121 | 0.130 |

DEPOSIT INFORMATION

A deposit, under the Budapest Treaty, of the lettuce cultivar seed of this invention has been made with American Type Culture Collection (ATCC), 10801 University Boulevard, Manassas, Va. 20110 on Aug. 2, 2002. The ATCC Accession number is PTA-4564.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant line and the like may be practiced within the scope of the invention, as limited only by the scope of the appended claims.

What is claimed is:

1. A seed of lettuce variety designated Sunbelt, representative seed having been deposited under ATCC Accession No. PTA-4564.

2. A lettuce plant, or a part thereof, produced by growing the seed of claim 1.

3. Pollen of the plant of claim 2.

4. An ovule of the plant of claim 2.

5. A tissue culture of regenerable cells produced from the plant of claim 2.

6. The tissue culture according to claim 5, wherein said cells of the tissue culture are produced from a tissue selected from the group consisting of leaves, pollen, embryos, cotyledons, a hypocotyl, meristematic cells, roots, root tips, anthers, flowers, seeds, and stems.

7. A lettuce plant regenerated from the tissue culture of claim 5, wherein the regenerated plant has all of the morphological and physiological characteristics of lettuce cultivar Sunbelt, representative seed of said lettuce cultivar Sunbelt having been deposited under ATCC Accession No. PTA-4564.

8. A method for producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 2.

9. A method of producing an herbicide resistant lettuce plant wherein the method comprises transforming the lettuce plant of claim 2 with a transgene that confers herbicide resistance.

10. An herbicide resistant lettuce plant produced by the method of claim 9.

11. A method of producing an insect resistant lettuce plant wherein the method comprises transforming the lettuce plant of claim 2 with a transgene that confers insect resistance.

12. An insect resistant lettuce plant produced by the method of claim 11.

13. A method of producing a disease resistant lettuce plant wherein the method comprises transforming the lettuce plant of claim 2 with a transgene that confers disease resistance.

14. A disease resistant lettuce plant produced by the method of claim 13.

15. A method of producing a lettuce plant with a value-added trait, wherein the method comprises transforming the lettuce plant of claim 2 with a transgene encoding a protein selected from the group consisting of a ferritin, a nitrate reductase and a monellin.

16. A lettuce plant with a value-added trait produced by the method of claim 15.

* * * * *